(12) United States Patent
Snyder et al.

(10) Patent No.: US 9,198,849 B2
(45) Date of Patent: Dec. 1, 2015

(54) SHAMPOO COMPOSITION COMPRISING LOW VISCOSITY EMULSIFIED SILICONE POLYMERS

(71) Applicant: The Procter & Gamble Company, Cincinnati, OH (US)

(72) Inventors: Michael Albert Snyder, Mason, OH (US); Joseph Harry Jansen, Harrison, OH (US); Roland Wagner, Bonn (DE); M. Janie Weaver, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/039,886

(22) Filed: Sep. 27, 2013

(65) Prior Publication Data

US 2015/0011449 A1   Jan. 8, 2015

Related U.S. Application Data

(60) Provisional application No. 61/842,640, filed on Jul. 3, 2013.

(51) Int. Cl.

| *C11D 9/36* | (2006.01) |
|---|---|
| *A61K 8/58* | (2006.01) |
| *A61Q 5/02* | (2006.01) |
| *A61K 8/893* | (2006.01) |
| *A61K 8/894* | (2006.01) |
| *A61K 8/898* | (2006.01) |

(52) U.S. Cl.
CPC ............... *A61K 8/585* (2013.01); *A61K 8/893* (2013.01); *A61K 8/894* (2013.01); *A61K 8/898* (2013.01); *A61Q 5/02* (2013.01)

(58) Field of Classification Search
CPC .... C11D 3/0026; C11D 3/373; C11D 3/3738; C11D 9/225; C11D 9/36
See application file for complete search history.

(56) References Cited

U.S. PATENT DOCUMENTS

| 4,529,586 A | 7/1985 | De Marco et al. |
|---|---|---|
| 4,533,714 A | 8/1985 | Sebag et al. |
| 4,587,321 A | 5/1986 | Sebag et al. |
| 4,597,962 A | 7/1986 | Grollier et al. |
| 4,673,568 A | 6/1987 | Grollier et al. |
| 4,833,225 A | 5/1989 | Schaefer et al. |
| 4,891,166 A | 1/1990 | Schaefer et al. |
| 4,902,499 A | 2/1990 | Bolish, Jr. et al. |
| 4,921,895 A | 5/1990 | Schaefer et al. |
| 5,098,979 A | 3/1992 | O'Lenick, Jr. |
| 5,153,294 A * | 10/1992 | O'Lenick, Jr. .................. 528/26 |
| 5,166,297 A | 11/1992 | O'Lenick, Jr. |
| 5,998,537 A | 12/1999 | Good et al. |
| 6,013,682 A | 1/2000 | Dalle et al. |
| 6,136,304 A | 10/2000 | Pyles |
| 6,207,141 B1 | 3/2001 | Pyles |
| 6,240,929 B1 | 6/2001 | Richard et al. |
| 6,242,554 B1 | 6/2001 | Busch et al. |
| 6,475,568 B1 | 11/2002 | Czech |
| 6,482,399 B2 | 11/2002 | Pyles |
| 6,482,969 B1 | 11/2002 | Helmrick et al. |
| 6,589,519 B1 | 7/2003 | Restle et al. |
| 6,607,717 B1 | 8/2003 | Johnson et al. |
| 6,610,280 B2 | 8/2003 | Ainger et al. |
| 6,649,689 B2 | 11/2003 | Gosselink et al. |
| 6,696,052 B2 | 2/2004 | Aeby et al. |
| 6,696,053 B1 | 2/2004 | Ma et al. |
| 6,730,766 B2 | 5/2004 | Schattenmann et al. |
| 6,903,061 B2 | 6/2005 | Masschelein et al. |
| 7,041,767 B2 | 5/2006 | Lange et al. |
| 7,087,650 B2 | 8/2006 | Lennon |
| 7,186,406 B2 | 3/2007 | Decoster et al. |
| 7,217,777 B2 | 5/2007 | Lange et al. |
| 7,223,384 B1 | 5/2007 | Decoster et al. |
| 7,235,749 B2 | 6/2007 | Imoto |
| 7,384,903 B2 | 6/2008 | Masschelein et al. |
| 7,390,479 B2 | 6/2008 | Sockel et al. |
| 7,563,856 B2 | 7/2009 | Lange et al. |
| 7,563,857 B2 | 7/2009 | Lange et al. |
| 7,585,494 B2 | 9/2009 | Lange et al. |
| 7,740,873 B2 | 6/2010 | Decoster et al. |
| 7,863,397 B2 | 1/2011 | Lange et al. |
| 8,076,442 B2 | 12/2011 | Moeller et al. |
| 8,362,185 B2 | 1/2013 | Wagner et al. |
| 2003/0143177 A1 | 7/2003 | Stella |
| 2004/0120914 A1 | 6/2004 | Decoster et al. |
| 2004/0126349 A1 | 7/2004 | Anderson et al. |

(Continued)

FOREIGN PATENT DOCUMENTS

| EP | 0490582 A1 | 6/1992 |
|---|---|---|
| EP | 1108416 B1 | 6/2006 |
| EP | 1093808 B1 | 7/2006 |
| EP | 1093809 B1 | 10/2006 |
| EP | 1093807 B1 | 4/2007 |
| EP | 1093805 B1 | 2/2008 |
| GB | 2161172 A | 1/1986 |
| WO | 99/32539 A1 | 7/1999 |
| WO | 00/07551 A1 | 2/2000 |
| WO | 01/41719 A1 | 6/2001 |
| WO | 01/41720 A1 | 6/2001 |

(Continued)

OTHER PUBLICATIONS

U.S. Appl. No. 14/498,215, filed Sep. 26, 2014, Snyder.
U.S. Appl. No. 14/498,246, filed Sep. 26, 2014, Snyder.

*Primary Examiner* — Charles Boyer
(74) *Attorney, Agent, or Firm* — James T. Fondriest

(57) ABSTRACT

A shampoo composition including (a) a silicone polymer including (i) one or more quaternary groups; (ii) at least one silicone block comprising greater than 200 siloxane units; (iii) at least one polyalkylene oxide structural unit; and (iv) at least one terminal ester group, and (b) a detersive surfactant. The silicone polymer has a viscosity of up to 100,000 mPa·s. The silicone polymer is a pre-emulsified dispersion with a particle size of less than about 1 micron.

14 Claims, No Drawings

(56) References Cited

U.S. PATENT DOCUMENTS

| | | |
|---|---|---|
| 2004/0265258 A1 | 12/2004 | Robinson et al. |
| 2005/0002871 A1 | 1/2005 | Ivanova et al. |
| 2005/0048016 A1 | 3/2005 | Lebreton et al. |
| 2005/0169878 A1 | 8/2005 | Elder et al. |
| 2006/0154848 A1 | 7/2006 | Girboux et al. |
| 2006/0233720 A1 | 10/2006 | Stork et al. |
| 2007/0041929 A1 | 2/2007 | Torgerson et al. |
| 2007/0286837 A1 | 12/2007 | Torgerson et al. |
| 2008/0029575 A1 | 2/2008 | Shelton et al. |
| 2008/0292575 A1 | 11/2008 | Uehara |
| 2012/0052038 A1 | 3/2012 | Panandiker et al. |
| 2013/0259817 A1* | 10/2013 | Uehara et al. ............. 424/70.11 |
| 2013/0259820 A1* | 10/2013 | Snyder et al. ............ 424/70.122 |
| 2015/0010487 A1 | 1/2015 | Snyder |
| 2015/0037273 A1 | 2/2015 | Wagner |
| 2015/0056155 A1 | 2/2015 | Wagner |

FOREIGN PATENT DOCUMENTS

| | | |
|---|---|---|
| WO | 01/41721 A1 | 6/2001 |
| WO | 0174312 A2 | 10/2001 |
| WO | 02/062311 A1 | 8/2002 |
| WO | 2004/039338 A1 | 5/2004 |
| WO | 2004/047779 A2 | 6/2004 |
| WO | 2004/069137 A1 | 8/2004 |
| WO | 2013/148935 A1 | 10/2013 |

* cited by examiner

SHAMPOO COMPOSITION COMPRISING LOW VISCOSITY EMULSIFIED SILICONE POLYMERS

FIELD OF THE INVENTION

Provided is a shampoo composition comprising (1) a silicone polymer containing quaternary groups and silicone blocks linked to alkylene oxides (e.g., ethylene oxide and/or propylene oxide), wherein the silicone polymer has a viscosity of up to 100,000 mPa·s, wherein the silicone polymer is a pre-emulsified dispersion with a particle size of less than about 1 micron; and (2) a detersive surfactant.

BACKGROUND OF THE INVENTION

Silicone polymers are strategically important materials in hair care, especially in providing conditioning benefits to hair. Human hair becomes damaged due to, for example, combing, permanent waves, and/or coloring the hair. Such damaged hair is often left hydrophilic and/or in a rough condition especially when the hair dries, compared to non-damaged or less damaged hair. Silicone polymers consisting of blocks of silicones and alkylene oxide (e.g., ethylene oxide and propylene oxide groups (EO/PO)) linked with amine- and quat-functional groups have been used to counteract the hydrophilic nature of damaged hair. Silicone blocks are responsible for conditioning and lubrication performance while amine- and quat-functional groups included in the polymer chain further aid deposition during rinsing. In particular, optimum conditioning performance has been observed for silicone blocks of greater than 200 D units. However these materials generally have high viscosities as neat materials. In order to achieve the desired conditioning benefits, these silicone polymers have traditionally been used in blends with silicone copolyols or other diluents or solvents.

Based on the foregoing, there is a need a shampoo composition which provides even greater improved conditioning benefits such as smooth feel and reduced friction on wet hair and dry hair. In addition, there is a need for a shampoo composition which provides improved conditioning benefits on damaged hair.

SUMMARY OF THE INVENTION

According to an embodiment of the invention, there is provided a shampoo composition comprising (a) a silicone polymer comprising: (i) one or more quaternary groups; (ii) at least one silicone block comprising greater than 200 siloxane units; (iii) at least one polyalkylene oxide structural unit; and (iv) at least one terminal ester group, wherein said silicone polymer has a viscosity of up to 100,000 mPa·s, wherein said silicone polymer is a pre-emulsified dispersion with a particle size of less than about 1 micron; and (b) a detersive surfactant.

According to another embodiment of the invention, there is provided a method of providing improved cleaning and conditioning benefits to hair and/or skin, the method comprising the step of washing said hair and/or skin with a shampoo composition comprising (a) a silicone polymer comprising: (i) one or more quaternary groups; (ii) at least one silicone block comprising greater than 200 siloxane units; (iii) at least one polyalkylene oxide structural unit; and (iv) at least one terminal ester group, wherein said silicone polymer has a viscosity of up to 100,000 mPa·s; and (b) a detersive surfactant.

These and other features, aspects, and advantages of the invention will become evident to those skilled in the art from a reading of the following disclosure.

DETAILED DESCRIPTION OF THE INVENTION

While the specification concludes with claims which particularly point out and distinctly claim the invention, it is believed that the provided invention will be better understood from the following description.

In all embodiments of the provided invention, all percentages are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at about 25° C. and at ambient conditions, wherein "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The processes of the provided invention can comprise, consist of, and consist essentially of the elements and limitations of the invention described herein, as well as any of the additional or optional ingredients, components, steps, or limitations described herein.

A. Silicone Polymer Containing Quaternary Groups

The compositions of the present invention comprise a low viscosity silicone polymer having a viscosity up to 100,000 mPa·s. Without being bound by theory, this low viscosity silicone polymer provides improved conditioning benefits over conventional silicones because of the addition of hydrophobic functionalities—quaternary amines, ethylene oxides/propylene oxides. Compared to previously disclosed silicones with quaternary functionality, these new structures are significantly lower in viscosity, so that they don't have to be blended with other lower viscosity diluents and dispersants to allow them to be formulated into products. Low viscosity silicone solvents and diluents can often cause viscosity and stability tradeoffs in shampoo products. The current invention eliminates the need for these materials since the silicone polymer is low enough in viscosity to be added directly or in emulsion form. The improved conditioning benefits include smooth feel, reduced friction, and prevention of hair damage, while, in some embodiments, eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present in an amount of from about 0.05% to about 15%, preferably from about 0.1% to about 10%, more preferably from about 0.15% to about 5%, and even more preferably from about 0.2% to about 4% by weight of the composition.

In a preferred embodiment the polyorganosiloxane compounds according to the invention have the general formulas (Ia) and (Ib):

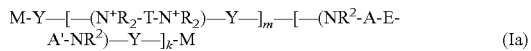 (Ia)

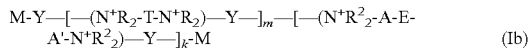 (Ib)

wherein:
- m is >0, preferred 0.01 to 100, more preferred 0.1 to 100, even more preferred 1 to 100, specifically 1 to 50, more specifically 1 to 20, even more specifically 1 to 10,
- k is 0 or an average value of from >0 to 50, or preferably from 1 to 20, or even more preferably from 1 to 10,
- M represents a terminal group, comprising terminal ester groups selected from
  —OC(O)—Z
  —OS(O)$_2$—Z
  —OS(O$_2$)O—Z
  —OP(O)(O—Z)OH
  —OP(O)(O—Z)$_2$
  wherein Z is selected from monovalent organic residues having up to 40 carbon atoms, optionally comprising one or more hetero atoms;
- A and A' each are independently from each other selected from a single bond or a divalent organic group having up to 10 carbon atoms and one or more hetero atoms, and
- E is a polyalkylene oxide group of the general formula:

—[CH$_2$CH$_2$O]$_q$—[CH$_2$CH(CH$_3$)O]$_r$-[CH$_2$CH(C$_2$H$_5$)O]$_s$— wherein q=0 to 200, r=0 to 200, s=0 to 200, and q+r+s=1 to 600.
- R$^2$ is selected from hydrogen or R,
- R is selected from monovalent organic groups having up to 22 carbon atoms and optionally one or more heteroatoms, and wherein the free valencies at the nitrogen atoms are bound to carbon atoms,
- Y is a group of the formula:

—K—S—K— and -A-E-A'- or -A'-E-A-, with S=

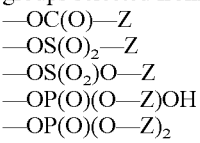

wherein R1=C$_1$-C$_{22}$-alkyl, C$_1$-C$_{22}$-fluoralkyl or aryl; n=200 to 1000, and these can be identical or different if several S Groups are present in the polyorganosiloxane compound;
- K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above,
- T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$-A-E-A'-NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds according to the invention.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise: (A) at least one polyorganosiloxane compound, comprising (i) at least one polyorganosiloxane group, (ii) at least one quaternary ammonium group, (iii) at least one terminal ester group, and (iv) at least one polyalkylene oxide group (as defined before); and (B) at least one polyorganosiloxane compound, comprising at least one terminal ester group, different from compound (A).

In the definition of component (A) it can be referred to the description of the polyorganosiloxane compounds of the invention. The polyorganosiloxane compound (B) differs from the polyorganosiloxane compound (A) preferably in that it does not comprise quaternary ammonium groups. Preferred polyorganosiloxane compounds (B) result from the reaction of monofunctional organic acids, in particular carboxylic acids, and polyorganosiloxane containing bisepoxides.

In the polyorganosiloxane compositions according to the invention the weight ratio of compound (A) to compound (B) is preferably less than 90:10. Or in other words, the content of component (B) is at least 10 weight percent. In a further preferred embodiment of the polyorganosiloxane compositions according to the invention in compound (A) the molar ratio of the quaternary ammonium groups (ii) and the terminal ester groups (iii) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 s$^{-1}$.

In addition to the above listed silicone polymers, preferred embodiments are provided below. For example, in the polyalkylene oxide group E of the general formula:

—[CH$_2$CH$_2$O]$_q$—[CH$_2$CH(CH$_3$)O]$_r$—[CH$_2$CH(C$_2$H$_5$)O]$_s$— wherein the q, r, and s indices may be defined as follows:
- q=0 to 200, or preferably from 0 to 100, or more preferably from 0 to 50, or even more preferably from 0 to 20,
- r=0 to 200, or preferably from 0 to 100, or more preferably from 0 to 50, or even more preferably from 0 to 20,
- s=0 to 200, or preferably from 0 to 100, or more preferably from 0 to 50, or even more preferably from 0 to 20,
- and q+r+s=1 to 600, or preferably from 1 to 100, or more preferably from 1 to 50, or even more preferably from 1 to 40.

For polyorganosiloxane structural units with the general formula S:

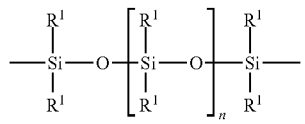

$R^1 = C_1$-$C_{22}$-alkyl, $C_1$-$C_{22}$-fluoralkyl or aryl; n=from 200 to 1000, or preferably from 300 to 500, K (in the group —K—S—K—) is preferably a bivalent or trivalent straight chain, cyclical or branched $C_2$-$C_{20}$ hydrocarbon residue which is optionally interrupted by —O—, —NH—, trivalent N, —NR$^1$—, —C(O)—, —C(S)—, and optionally substituted with —OH.

In specific embodiments, $R^1$ is $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ is more preferably $C_1$-$C_6$ alkyl, $C_1$-$C_6$ fluoroalkyl, even more preferably $C_1$-$C_4$ fluoroalkyl, and phenyl. Most preferably, $R^1$ is methyl, ethyl, trifluoropropyl and phenyl.

As used herein, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, CF$_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

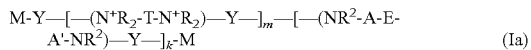

(Ia)

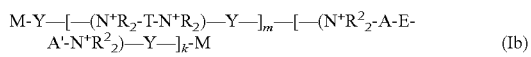

(Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

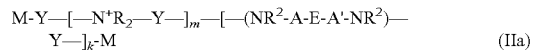

(IIa)

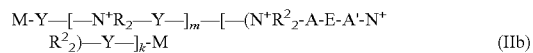

(IIb)

wherein each group is as defined above. Also in such formula the repeating units are usually in a statistical arrangement (i.e not a block-wise arrangement).

wherein, as defined above, M is
—OC(O)—Z,
—OS(O)$_2$—Z
—OS(O$_2$)O—Z
—OP(O)(O—Z)OH
—OP(O)(O—Z)$_2$ Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or preferably between 20:1 and 1:20, or more preferably between 10:1 and 1:10.

In the group —(N$^+$R$_2$-T-N$^+$R$_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Further performance improvements can be achieved by pre-dispersing the silicone polymer in a small particle emulsion (less than 1 micron) prior to adding it to the shampoo base.

The term "emulsion" in this patent application describes any stable emulsion or dispersion of the silicone polymer, separately prepared and used as one of the components of a shampoo composition.

Stable means that the viscosity, particle size, and other important characteristics of the emulsion do not significantly change over reasonable time under exposure to typical temperature, moisture, pressure, shear, light and other environmental conditions that the pre-emulsion is exposed during packing, storage, and transportation Making the small particle emulsion may require pre-emulsifying the silicone polymer before their addition to the shampoo composition. A non-limiting example of a method of making is provided below. All oil soluble components are mixed in a vessel. Heat may be applied to allow mixture to liquidify. All water soluble components are mixed in a separate vessel and heated to about same temperature as the oil phase. The oil phase and aqueous phase are mixed under a high shear mixer (example, Turrax mixer by IKA) The particle size of the conditioning active is in the range of 0.01-5 μm, more preferred 0.05-1 μm, most preferred 0.1-0.5 μm. High energy mixing device may be used to achieve desired particle size. High energy mixing device include, but not limited to Microfluidizer from Microfluidics Corp., Sonolator from Sonic Corp., Colloid mill from Sonic Corp.

The emulsifiers which may be selected for each the silicone may be guided by the Hydrophilic-iUpophilic-Balance value (HLB value) of emulsifiers. Suitable range of HLB value may be 6-16, alternatively 8-14. Emulsifiers with a HLB higher than 10 are water soluble. Emulsifiers with low HLB are lipid soluble. To obtain suitable HLB value, a mixture of two or more emulsifiers may be used. Suitable emulsifiers include non-ionic, cationic, anionic and amphoteric emulsifiers.

The concentration of the emulsifier in the emulsion should be sufficient to provide desired the emulsification of the conditioning active to achieve desired particle size and emulsion stability, and generally ranges from about 0.1 wt %-about 50 wt %, from about 1 wt %-about 30 wt %, from about 2 wt %-about 20 wt %, for example.

The use of a pre-emulsified dispersion of the silicone may present multiple advantages including: (i) The small particle size of the silicones in the emulsion leads to more even deposition and reduces island-like spotty deposits; and (ii) the more even deposition is more favorable for providing smoothness for hair/skin surfaces, easier combing, and enhanced hair volume.

B. Detersive Surfactant

The shampoo composition of the present invention includes a detersive surfactant, which provides cleaning performance to the composition. The detersive surfactant in turn comprises an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, or from about 10 wt % to about 20 wt %. Accordingly, the shampoo composition may comprise a detersive surfactant in an amount of about 5 wt %, about 10 wt %, about 12 wt %, about 15 wt %, about 17 wt %, about 18 wt %, or about 20 wt %, for example.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

In an embodiment, the composition comprises an anionic surfactant and a non-ionic co-surfactant. In another embodiment the surfactant system is free, or substantially free of sulfate materials. Suitable sulfate free surfactants are disclosed in WO publication 2011/120780 and WO publication 2011/049932.

C. Deposition Polymer

The shampoo composition may also comprise a cationic deposition polymer. These cationic deposition polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic deposition polymer can be a mixture of deposition polymers.

(1) Cationic Guar Polymers

According to an embodiment of the present invention, the shampoo composition comprises a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

According to one embodiment, the cationic guar polymer has a weight average M.Wt. of less than about 2.5 million g/mol, and has a charge density of from about 0.05 meq/g to about 2.5 meq/g. In an embodiment, the cationic guar polymer has a weight average M.Wt. of less than 1.5 million g/mol, or from about 150 thousand to about 1.5 million g/mol, or from about 200 thousand to about 1.5 million g/mol, or from about 300 thousand to about 1.5 million g/mol, or from about 700,000 thousand to about 1.5 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula 1:

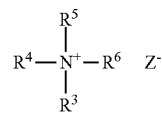

wherein where $R^3$, $R^4$ and $R^5$ are methyl or ethyl groups; $R^6$ is either an epoxyalkyl group of the general formula 2:

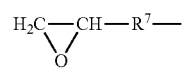

or $R^6$ is a halohydrin group of the general formula 3:

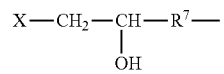

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula 4:

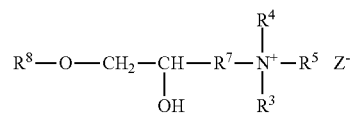

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

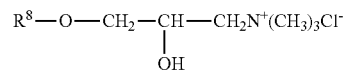

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). Other suitable guar hydroxypropyltrimonium chloride are: guar hydroxypropyltrimonium chloride which has a charge density of about 1.1 meq/g and a M.Wt. of about 500,000 g/mole is available from ASI, a charge density of about 1.5 meq/g and a M.Wt. of about 500,000 g/mole is available from ASI.

Other suitable guar hydroxypropyltrimonium chloride are: Hi-Care 1000, which has a charge density of about 0.7 meq/g and a M.Wt. of about 600,000 g/mole and is available from Rhodia; N-Hance 3269 and N-Hance 3270, which has a charge density of about 0.7 meq/g and a M.Wt. of about 425,000 g/mole and is available from ASI; N-Hance 3196, which has a charge density of about 0.8 and a M. Wt. Of about 1,100,000 g/mole and is available from ASI. AquaCat CG518 has a charge density of about 0.9 meq/g and a M.Wt. of about 50,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

(2) Cationic Non-Guar Galactomannan Polymers

The shampoo compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

In one embodiment of the invention, the non-guar galactomannan polymer derivatives have a M. Wt. from about 1,000 to about 10,000,000, and/or form about 5,000 to about 3,000, 000.

The shampoo compositions of the present invention may include galactomannan polymer derivatives which have a cationic charge density from about 0.5 meq/g to about 7 meq/g. In one embodiment of the present invention, the galactomannan polymer derivatives have a cationic charge density from about 1 meq/g to about 5 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

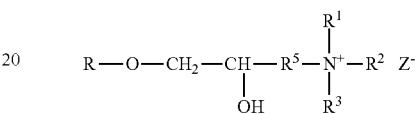

wherein R is the gum. The cationic galactomannan derivative can be a gum hydroxypropyltrimethylammonium chloride, which can be more specifically represented by the general formula 7:

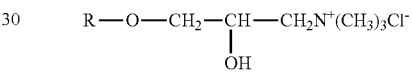

In another embodiment of the invention, the galactomannan polymer derivative is an amphoteric galactomannan polymer derivative having a net positive charge, obtained when the cationic galactomannan polymer derivative further comprises an anionic group.

In one embodiment of the invention the cationic non-guar galactomannan has a ratio of mannose to galactose is greater than about 4:1, a M. Wt. of about 100,000 to about 500,000, and/or from about 150,000 to about 400,000 and a cationic charge density from about 1 meq/g to about 5 meq/g, and/or from 2 meq/g to about 4 meq/g and is a derived from a *cassia* plant.

The shampoo compositions of the present invention may comprise at least about 0.05% of a galactomannan polymer derivative by weight of the composition. In one embodiment of the present invention, the shampoo compositions comprise from about 0.05% to about 2%, by weight of the composition, of a galactomannan polymer derivative.

(3) Cationically Modified Starch Polymer

The shampoo compositions of the present invention may comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions of the present invention may comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the shampoo compositions of the present invention may have a molecular weight from about 850,000 to about 15,000,000 and/or from about 900,000 to about 5,000,000. As used herein, the term "molecular weight" refers to the weight average molecular weight. The weight average molecular weight may be measured by gel permeation chromatography ("GPC") using a Waters 600E HPLC pump and Waters 717 auto-sampler equipped with a Polymer Laboratories PL Gel MIXED-A GPC column (Part Number 1110-6200, 600.times.7.5 mm, 20 um) at a column temperature of 55.degree. C. and at a flow rate of 1.0 ml/min (mobile phase consisting of Dimethylsulfoxide with 0.1% Lithium Bromide), and using a Wyatt DAWN EOS MALLS (multi-angle laser light scattering detector) and Wyatt Optilab DSP (interferometric refractometer) detectors arranged in series (using a dn/de of 0.066), all at detector temperatures of 50° C., with a method created by using a Polymer Laboratories narrow dispersed Polysaccharide standard (Mw=47,300), with an injection volume of 200 µl.

The shampoo compositions of the present invention may include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers may have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch may be one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch may be available from known starch suppliers. Also suitable for use in the present invention is nonionic modified starch that could be further derivatized to a cationically modified starch as is known in the art. Other suitable modified starch starting materials may be quaternized, as is known in the art, to produce the cationically modified starch polymer suitable for use in the invention.

(4) Cationic Copolymer of an Acrylamide Monomer and a Cationic Monomer

According to an embodiment of the present invention, the shampoo composition may comprise a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer comprises:
(i) an acrylamide monomer of the following Formula AM:

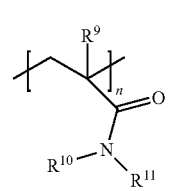

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula CM:

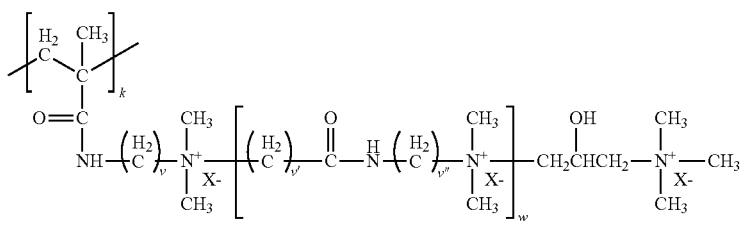

Formula CM where k=1, each of v, v', and v" is independently an integer of from 1 to 6, w is zero or an integer of from 1 to 10, and X⁻ is an anion.

In an embodiment, cationic monomer conforming to Formula CM and where k=1, v=3 and w=0, z=1 and X⁻ is Cl⁻ to form the following structure:

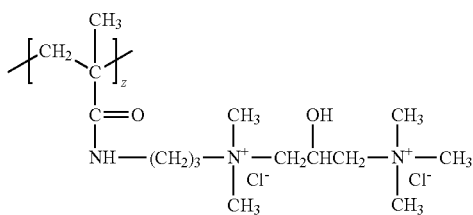

The above structure may be referred to as diquat. In another embodiment, the cationic monomer conforms to Formula CM and wherein v' and v" are each 3, v=1, w=1, y=1 and X⁻ is Cl⁻, such as:

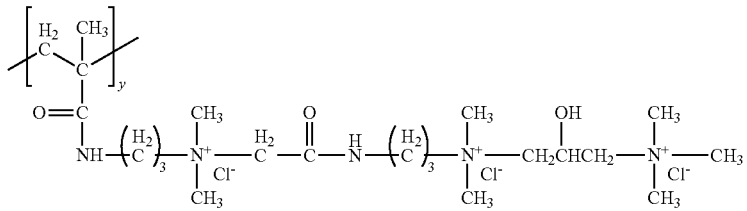

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium, N-[2-[[[dimethyl[3-[(2-methyl-1-oxo-2-propenyl)amino]propyl]ammonio]acetyl]amino]ethyl]2-hydroxy-N,N,N',N,N-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

In an embodiment, the cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. In an embodiment, the cationized esters of the (meth)acrylic acid containing a quaternized N atom are selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl (meth)acrylamide with C1 to C3 in the alkyl and alkylene groups. In an embodiment, the cationic monomer based on a (meth)acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl (meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl (meth)acrylate quaternized with methyl chloride (ADAME-Q) and 3-dimethylammoniumpropyl (meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

(5) Cationic Synthetic Polymer

According to an embodiment of the present invention, the shampoo composition may comprise a cationic synthetic polymer that may be formed from
  i) one or more cationic monomer units, and optionally
  ii) one or more monomer units bearing a negative charge, and/or
  iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers In one embodiment, the cationic polymers are water soluble or dispersible, non-crosslinked, synthetic cationic polymers having the following structure:

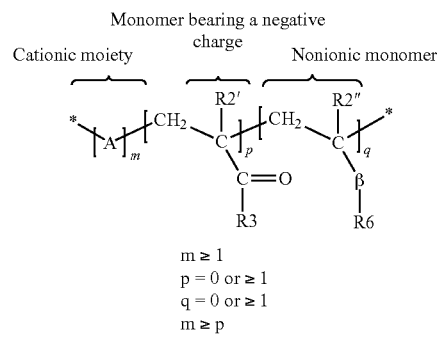

$m \geq 1$
$p = 0$ or $\geq 1$
$q = 0$ or $\geq 1$
$m \geq p$ where A, may be one or more of the following cationic moieties:

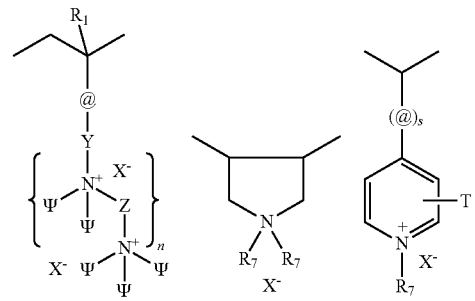

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or ≤1;
where T and R7=C1-C22 alkyl; and
where X⎯=halogen, hydroxide, alkoxide, sulfate or alkylsulfate.

Where the monomer bearing a negative charge is defined by R2'=H, C1-C4 linear or branched alkyl and R3 as:

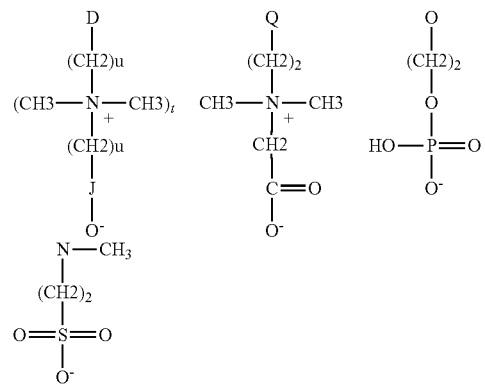

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

where G' and G' are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth) acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula $-NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropane-sulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

In one embodiment, the cationic polymer described herein aids in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable shampoo composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. In some embodiments, the cationic charge density is about 6.2 meq/gm. The polymers also have a M. Wt. of from about 1,000 to about 5,000,000, and/or from about 10,000 to about 2,000,000, and/or from about 100,000 to about 2,000,000.

In another embodiment of the invention cationic synthetic polymers that provide enhanced conditioning and deposition of benefit agents but do not necessarily form lytropic liquid crystals have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 5,000,000, from about 10,000 to about 2,000,000, and from about 100,000 to about 2,000,000.

The concentration of the cationic polymers ranges about 0.025% to about 5%, from about 0.1% to about 3%, and/or from about 0.2% to about 1%, by weight of the shampoo composition.

(6) Cationic Cellulose Polymers

Suitable cationic cellulose polymers may be salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

In an embodiment, the shampoo composition may comprise a plurality of cationic conditioning polymers. According to one embodiment, where two cationic conditioning polymers are present, the weight ratio of a first cationic conditioning polymer to a second cationic conditioning polymer is from about 1000:1 to about 2:1. In an embodiment, the weight ratio of the first cationic conditioning polymer to the second cationic conditioning polymer is from about 1000:1 to about 4:1. In an embodiment, weight ratio of the first cationic conditioning polymer to the second cationic conditioning polymer is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1.

D. Carrier

The shampoo compositions can be in the form of pourable liquids (under ambient conditions). Such compositions may comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in embodiments of the shampoo compositions of the present invention includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

E. Optional Ingredients

In accordance with embodiments of the present invention, the shampoo composition may further comprise one or more optional ingredients, including benefit agents Suitable benefit agents include, but are not limited to conditioning agents, silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

1. Silicones

The shampoo composition may further comprise one or more silicone conditioning agents in addition to the silicone quaternary polymers disclosed in Section A. The additional silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant.

Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

2. Organic Conditioning Materials

The shampoo composition may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

3. Emulsifiers

A variety of anionic and nonionic emulsifiers can be used in the shampoo composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

4. Chelating Agents

The shampoo composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the shampoo compositions can be as low as about 0.01 wt % or even as high as about 10 wt %, but above the higher level (i.e., 10 wt %) formulation and/or human safety concerns may arise. In an embodiment, the level of the EDDS chelant may be at least about 0.05 wt %, at least about 0.1 wt %, at least about 0.25 wt %, at least about 0.5 wt %, at least about 1 wt %, or at least about 2 wt % by weight of the shampoo composition. Levels above about 4 wt % can be used but may not result in additional benefit.

5. Anti-Dandruff Agent

According to an embodiment, the shampoo composition comprises an anti-dandruff active, which may be an anti-dandruff active particulate. The anti-dandruff active can be selected from the group consisting of: pyridinethione salts; azoles, such as an imidazole such as ketoconazole, econazole, climbazole and elubiol; selenium sulphide; coal tar, particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

The anti-dandruff active can also be selected from polyvalent metal salts of pyrithione, the composition further comprises one or more anti-fungal and/or anti-microbial actives.

Embodiments of the present invention may also comprise a combination of anti-microbial actives.

In an embodiment, the composition comprises an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material (ZLMs), by total weight of the composition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides or hydroxy double salts. In an embodiment, the composition comprises basic zinc carbonate. Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

6. Gel Networks

The shampoo composition may also comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to hair compositions. In addition, they deliver conditioned feel benefits.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 3 provides the components and their respective amounts for the gel network composition.

TABLE 3

Gel network components

| Ingredient | Wt. % |
|---|---|
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

Product Form

The shampoo compositions of the present invention may be presented in typical shampoo formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos, and treatment products; and any other form that may be applied to hair.

According to one embodiment, the shampoo compositions may be provided in the form of a porous, dissolvable solid structure having a percent open cell content of from about 80% to about 100%, such as those disclosed in U.S. Patent Application Publication Nos. 2009/0232873; and 2010/0179083, which are incorporated herein by reference in their entirety.

The shampoo composition can have a viscosity of 4,000 cP to 20,000 cP, or from about 6,000 cP to about 12,000 cP, or from about 8,000 cP to about 11,000 cP, measured at 26.6° C. with a Brookfield R/S Plus Rheometer at 2 $s^{-1}$. cP means centipoises.

Method of Making

The shampoo compositions are generally prepared by conventional. Such methods include mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The shampoo composition may be in a single phase or a single product, or the shampoo composition may be in a separate phases or separate products. If two products are used, the products may be used together, at the same time or sequentially.

Method of Use

The shampoo compositions of the present invention can be applied to the hair and rinsed off with water.

EXAMPLES

The exemplified compositions can be prepared by conventional formulation and mixing techniques. It will be appreciated that other modifications of the hair care composition within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Table 1 includes examples of specific structures for the silicone quaternary polymers described in Section A of this application.

TABLE 1

| Variable | Silicone Quaternary Polymer A | Silicone Quaternary Polymer B | Silicone Quaternary Polymer C | Silicone Quaternary Polymer D | Silicone Quaternary Polymer E |
|---|---|---|---|---|---|
| M | lauric ester | lauric ester | lauric ester | lauric ester | lauric ester |
| Y | K—S—K | K—S—K | K—S—K | K—S—K | K—S—K |
| K | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ |
| S | PDMS block with 368 siloxane units | PDMS block with 368 siloxane units | PDMS block with 368 siloxane units | PDMS block with 450 siloxane units | PDMS block with 368 siloxane units |
| R, $R^2$ | methyl | methyl | methyl | methyl | methyl |
| T | $C_6H_{12}$ | $C_6H_{12}$ | $C_6H_{12}$ | $C_6H_{12}$ | $C_6H_{12}$ |
| A | $CH_2$—COO— | $CH_2$—COO— | $CH_2$—COO— | $CH_2$—COO— | $CH_2$—COO— |
| A' | CO—$CH_2$ | CO—$CH_2$ | CO—$CH_2$ | CO—$CH_2$ | CO—$CH_2$ |
| E | Ethylene oxide ($CH_2$—$CH_2$—O) with average degree of ethoxylation of 2 | Ethylene oxide ($CH_2$—$CH_2$—O) with average degree of ethoxylation of 34 | Propylene oxide ($CH_2$—$CH(CH_3)$—O) with average degree of propoxylation of 3.5 | Propylene oxide ($CH_2$—$CH(CH_3)$—O) with average degree of propoxylation of 3.5 | Ethylene oxide ($CH_2$—$CH_2$—O) with average degree of ethoxylation of 2 |
| Ratio of silicone blocks:alkylene oxide blocks | 1:1 | 9:1 | 9:1 | 9:1 | 7:3 |
| Total Viscosity | 4700 mPa·s | 2800 mPa·s | 2600 mPa·s. | 5400 mPa·s. | 6000 mPa·s. |

The following examples in Table 2 illustrate embodiments of silicone emulsions as described in Section A of this Application.

TABLE 2

| | Silicone Emulsion | | | | |
|---|---|---|---|---|---|
| | A | B | C | D | E |
| Water | q.s. | q.s. | q.s. | q.s. | q.s. |
| Sodium Laureth Sulfate [1] | 5.0 | — | — | 5.0 | 5.0 |
| C11-15 Pareth-5 [2] | — | 1.4 | 1.0 | — | — |
| C11-15 Pareth-12 [3] | — | 2.0 | — | — | — |
| Silicone Quaternary Polymer A | 20.0 | | | | |
| Silicone Quaternary Polymer B | | 10.0 | | | |
| Silicone Quaternary Polymer C | | | 10.0 | | |
| Silicone Quaternary Polymer D | | | | 20.0 | |
| Silicone Quaternary Polymer E | | | | | 20.0 |

[1] Sodium Laureth-1 Sulfate, from Stepan
[2] Tergitol 15-S-5, from The Dow Chemical Company
[3] Tergitol 15-S-12, from The Dow Chemical Company The following examples in Table 3 illustrate embodiments of the present invention wherein the silicone polymer is emulsified.

TABLE 3

| | 11 | 12 | 13 | 14 | 15 | 16 | 17 | 18 | 19 | 20 |
|---|---|---|---|---|---|---|---|---|---|---|
| Water | q.s. | q.s. | q.s. | q.s. | q.s. | q.s. | q.s. | q.s. | q.s. | q.s. |
| Sodium Laureth Sulfate [1] | 13.0 | 12.0 | 10.5 | 10.5 | 10.5 | 10.5 | 10.5 | 12.0 | 12.0 | 12.0 |
| Sodium Lauryl Sulfate [2] | 1.5 | 1.5 | 1.5 | 1.5 | 1.5 | 1.5 | 1.5 | 1.5 | 1.5 | 1.5 |
| CMEA [3] | — | — | 0.8 | — | — | — | 0.8 | — | — | — |
| Cocoamidopropyl Betaine [4] | 1.7 | 1.7 | 1.0 | 1.0 | 1.0 | 1.0 | 1.0 | 1.7 | 1.7 | 1.0 |
| Guar Hydroxypropyl Trimonium Chloride [5] | 0.325 | 0.3 | — | — | — | — | — | 0.30 | — | — |
| Polyquaternium-10 [6] | 0.075 | — | — | — | — | — | — | — | 0.30 | — |
| Polyquaternium-6 [7] | 0.075 | — | 0.25 | — | — | — | — | — | — | — |
| Silicone Emulsion A | 5.0 | | | | | 2.5 | | | | |
| Silicone Emulsion B | | 3.75 | | | | | 2.5 | | | |
| Silicone Emulsion C | | | 2.5 | | | | | 5.0 | | |

TABLE 3-continued

|  | 11 | 12 | 13 | 14 | 15 | 16 | 17 | 18 | 19 | 20 |
|---|---|---|---|---|---|---|---|---|---|---|
| Silicone Emulsion D |  |  |  | 5.0 |  |  |  |  | 1.25 |  |
| Silicone Emulsion E |  |  |  |  | 1.25 |  |  |  |  | 3.75 |
| Glycerine [8] | 0.5 | 0.5 | — | — | — | — | — | — | — | — |
| EGDS [9] | — | — | 1.5 | — | — | — | 1.5 | — | — | — |
| Trihydroxystearin [10] | 0.1 | 0.1 | — | 0.1 | 0.1 | 0.1 | — | 0.1 | 0.1 | 0.1 |
| Fragrance, preservatives, viscosity adjustment | Up to 3% | Up to 3% | Up to 3% | Up to 3% | Up to 3% | Up to 3% | Up to 3% | Up to 3% | Up to 3% | Up to 3% |

[1] Sodium Laureth-1 Sulfate, from Stepan
[2] Sodium Lauryl Sulfate, from P&G
[3] Ninol Comf, from Stepan
[4] Amphosol HCA-B, from Stepan
[5] NHance-3196, from ASI
[6] Ucare Polymer KG-30M, from The Dow Chemical Company
[7] Mirapol 100, from Rhodia Inc.
[8] Superol V Glycerine USP, from P&G
[9] EGDS pure, from Evonik
[10] Thixcin R from Elementis Data Referring to Table 4, Applicants have surprisingly found that Applicants' emulsified silicone polymer (QAS 4996) in shampoo shows statistically significant improved dry conditioning performance when compared to corresponding emulsified polydimethylsilicone (PDMS) benchmarks.

TABLE 4

| Composition | Friction Force (g) | |
|---|---|---|
| Shampoo with 1% Silicone Quaternary Polymer C - milled emulsion | 218.97 | A |
| Shampoo with 1% PDMS (330,000 cs) - milled emulsion | 237.63 | B |
| Shampoo with 1% PDMS (5,000 cs) - milled emulsion | 259.74 | B |

*Compositions sourced from Momentive Performance Materials

The measurements in Table 4 were taken by measuring the friction force (g) using the Instron Friction Method (IFM).

Instron Friction Method (IFM)

Dry conditioning performance is evaluated by hair friction force measured by an instrument named Instron Tester (Instron Mini 55, Instron, Inc.; Canton, Mass., USA).

First, a 20 g hair switch is cleaned with tap water running at about 1.5 gpm at about 100° F.

2 ml of Pantene Fine Hair Solutions Flat to Volume Shampoo is then applied to the hair switch using a syringe, applying half of the syringe to the front and half of the syringe to the back of the switch.

The Flat to Volume Shampoo is then massaged into the hair using a milking motion with a thumb on the front of the switch and fingers on the back for 30 seconds.

The switch is then rinsed with tap water running at about 1.5 gpm at about 100° F. for 30 seconds while massaging the hair using a milking motion with a thumb on the front and fingers on the back of the switch.

The shampoo procedure is repeated.

2 ml of the shampoo comprising a conditioning composition is then applied to the hair using a syringe, applying half of the syringe to the front and half of the syringe to the back of the switch.

The conditioning composition is then massaged into the hair using a milking motion with a thumb on the front of the switch and fingers on the back for 30 seconds.

The switch is allowed to rest for 30 seconds.

The hair switch is then rinsed with tap water running at about 1.5 gpm at about 100° F. for 30 seconds while massaging the hair using a milking motion with a thumb on the front and fingers on the back of the switch.

Excess water is removed from the switch by using fingers as a squeegee, running the fingers down the switch twice.

The switch is hung on a cart and taken to a CT/CH room set at about 70° F. and about 50% room humidity to dry and equilibrate overnight.

The friction force (g) between the hair surface and a foam pad along the hair is measured using the Instron Mini 55.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a) a silicone polymer comprising:
      i. one or more quaternary groups;
      ii. at least one silicone block comprising greater than 200 siloxane units;
      iii. at least one polyalkylene oxide structural unit; and
      iv. at least one terminal ester group
      wherein said silicone polymer has a viscosity of up to 100,000 mPa·s, wherein said silicone polymer is a pre-emulsified dispersion with a particle size of less than about 1 micron, and b) a detersive surfactant.

2. The shampoo composition of claim 1, wherein said silicone block comprises from about 300 to about 600 siloxane units.

3. The shampoo composition of claim 1, wherein said silicone polymer is present in an amount of from about 0.05% to about 15% by weight of the composition.

4. The shampoo composition of claim 1, wherein said silicone polymer is present in an amount of from about 0.1% to about 10% by weight of the composition.

5. The shampoo composition of claim 1, wherein said silicone polymer is present in an amount of from about 0.15% to about 5% by weight of the composition.

6. The shampoo composition of claim 1, wherein said silicone polymer is defined by the following chemical structure:

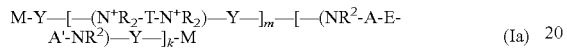 (Ia)

wherein:
m is an average value of from above 0 to 100
k is an average value of from above 0 to 50
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms,
wherein A and A' each are independently selected from a single bond or a divalent organic group having up to 10 carbon atoms and one or more hetero atoms, and
E is a polyalkylene oxide group of the general formula:

with
q=0 to 200,
r=0 to 200,
s=0 to 200,
and q+r+s=1 to 600,
R is selected from monovalent organic groups having up to 22 carbon atoms and optionally one or more heteroatoms, and wherein the free valencies at the nitrogen atoms are bound to carbon atoms, $R^2$ is selected from hydrogen or R,
Y is a group of the formula:

with
S=

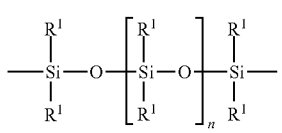

wherein $R^1$=$C_1$-$C_{22}$-alkyl, $C_1$-$C_{22}$-fluoralkyl or aryl,
n=200 to 1000,
K is a bivalent or trivalent straight chain, cyclic and/or branched $C_2$-$C_{40}$ hydrocarbon residue which is optionally interrupted by —O—, —NH—, trivalent N, —$NR^1$—, —C(O)—,
—C(S)—, and optionally substituted with —OH,
wherein T is selected from a divalent organic group having up to 20 carbon atoms and one or more hetero atoms.

7. The shampoo composition of claim 6, wherein the K residues in said —K—S—K— moiety are identical or different, and are bound to the silicon atom of the residue S via a C—Si-bond.

8. The shampoo composition of claim 1, wherein said silicone polymer is defined by the following chemical structure:

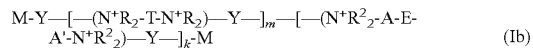 (Ib)

wherein:
m is an average value of from above 0 to 100
k is an average value of from above 0 to 50
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms,
wherein A and A' each are independently selected from a single bond or a divalent organic group having up to 10 carbon atoms and one or more hetero atoms, and
E is a polyalkylene oxide group of the general formula:

with
q=0 to 200,
r=0 to 200,
s=0 to 200,
and q+r+s=1 to 600,
R is selected from monovalent organic groups having up to 22 carbon atoms and optionally one or more heteroatoms, and wherein the free valencies at the nitrogen atoms are bound to carbon atoms, $R^2$ is selected from hydrogen or R,\
Y is a group of the formula:

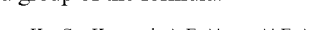

with
S=

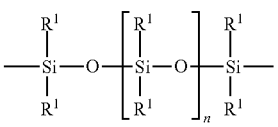

wherein $R^1$=$C_1$-$C_{22}$-alkyl, $C_1$-$C_{22}$-fluoralkyl or aryl,
n=200 to 1000,
K is a bivalent or trivalent straight chain, cyclic and/or branched $C_2$-$C_{40}$ hydrocarbon residue which is optionally interrupted by —O—, —NH—, trivalent N, —$NR^1$—, —C(O)—,
—C(S)—, and optionally substituted with —OH,
wherein T is selected from a divalent organic group having up to 20 carbon atoms and one or more hetero atoms.

9. The shampoo composition of claim 8, wherein the K residues in said —K—S—K— moiety are identical or different, and are bound to the silicon atom of the residue S via a C—Si-bond.

10. The shampoo composition of claim 8 wherein:
m is >0 to 10,
k is >0 to 10,
M is —OC(O)—Z,
Z is hydrocarbon chain with 0 to 40 carbons q=0-50, r=0-50, q+r is at least 1, s=0,
$R^2$ is methyl
n=300-500.

11. The shampoo composition of claim 1, wherein said silicone polymer has a viscosity of from 500 to 50,000 mPa·s.

12. The shampoo composition of claim 1, wherein said silicone polymer has a viscosity of from 500 to 5000 mPa·s.

13. The shampoo composition of claim 1, wherein said detersive surfactant is present in an amount of from about 0.5% to about 20% by weight of the composition.

14. A method of providing improved cleaning and conditioning benefits to hair and/or skin, said method comprising the step of washing said hair and/or skin with said shampoo composition of claim 1.

* * * * *